US00PP15270P2

(12) United States Plant Patent
Unger

(10) Patent No.: US PP15,270 P2
(45) Date of Patent: Oct. 26, 2004

(54) ***PENTAS* PLANT NAMED 'LAVA WHITE'**

(50) Latin Name: *Pentas lanceolata*
Varietal Denomination: Lava White

(75) Inventor: Helmut Unger, Rheinfelden (DE)

(73) Assignee: John Bodger & Sons Co., South El Monte, CA (US)

( * ) Notice: Subject to any disclaimer, the term of this patent is extended or adjusted under 35 U.S.C. 154(b) by 0 days.

(21) Appl. No.: 10/747,786

(22) Filed: Dec. 29, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A new and distinct cultivar of *Pentas* plant named 'Lava White', characterized by its upright and somewhat outwardly spreading plant habit; freely branching habit; dark green-colored leaves; freely flowering habit; and white-colored flowers arranged in large terminal corymbs that are positioned above the foliage.

1 Drawing Sheet

Botanical classification/cultivar designation: *Pentas lanceolata* cultivar Lava White.

BACKGROUND OF THE INVENTION

The present Invention relates to a new and distinct cultivar of *Pentas* plant, botanically known as *Pentas lanceolata,* and hereinafter referred to by the name 'Lava White'.

The new *Pentas* is a product of a planned breeding program conducted by the Inventor in Rheinfelden, Germany. The objective of the breeding program was to develop new moderately tall *Pentas* cultivars with numerous flowers and attractive flower and foliage coloration.

The new *Pentas* originated from a cross-pollination made by the Inventor during the summer of 1999 of two unnamed proprietary selections of *Pentas lanceolata,* not patented. The cultivar Lava White was discovered and selected by the Inventor as a flowering plant within the progeny of the stated cross-pollination in a controlled environment in Rheinfelden, Germany.

Asexual reproduction of the new cultivar by terminal cuttings taken in Rheinfelden, Germany, has shown that the unique features of this new *Pentas* are stable and reproduced true to type in successive generations of asexual reproduction.

SUMMARY OF THE INVENTION

The following traits have been repeatedly observed and are determined to be the unique characteristics of 'Lava White'. These characteristics in combination distinguish 'Lava White' as a new and distinct *Pentas* cultivar:

1. Upright and outwardly spreading plant habit.
2. Freely branching habit.
3. Dark green-colored leaves.
4. Freely flowering habit.
5. White-colored flowers arranged in large terminal corymbs that are positioned above the foliage.

Plants of the new *Pentas* differ primarily from plants of the parent selections in the following characteristics:

1. Plants of the new *Pentas* are more compact than plants of the parent selections.

2. Plants of the new *Pentas* have larger flowers and larger inflorescences than plants of the parent selections.
3. Flowers of plants of the new *Pentas* are not fragrant whereas flowers of plants of the parent selections are fragrant.

The new *Pentas* can be compared to the *Pentas lanceolata* cultivar New Look Red, not patented. However, in side-by-side comparisons conducted in Rheinfelden, Germany, plants of the new *Pentas* differed from plants of the cultivar New Look Red in the following characteristics:

1. Plants of the new *Pentas* were taller and more vigorous than plants of the cultivar New Look Red.
2. Plants of the new *Pentas* were more uniform than plants of the cultivar New Look Red.
3. Flowers of plants of the new *Pentas* and the cultivar New Look Red differed in flower coloration.

The new *Pentas* can also be compared to the *Pentas lanceolata* cultivar New Look White, not patented. However, in side-by-side comparisons conducted in Rheinfelden, Germany, plants of the new *Pentas* differed from plants of the cultivar New Look White in the following characteristics:

1. Plants of the new *Pentas* were taller and more vigorous than plants of the cultivar New Look White.
2. Plants of the new *Pentas* had larger inflorescences than plants of the cultivar New Look White.
3. Plants of the new *Pentas* were more uniform than plants of the cultivar New Look White.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Pentas.*

The photograph at the top of the sheet comprises a side perspective view of a flowering plant of 'Lava White' grown in a container.

The photograph at the bottom of the sheet is a close-up view of typical flowers, inflorescences and leaves of 'Lave White'.

DETAILED BOTANICAL DESCRIPTION

Plants of the cultivar Lava White have not been observed under all possible environmental conditions. The phenotype may vary somewhat with variations in environment such as temperature and light intensity, without, however, any variance in genotype. The aforementioned photographs and following observations and measurements describe plants grown in Lompoc, Calif., under commercial practice in a polycarbonate-covered greenhouse during the summer. During the production of the plants, day temperatures ranged from 21 to 27° C., night temperatures ranged from 16 to 18° C. and light levels ranged from 5,000 to 9,000 foot-candles. Rooted young plants were pinched once and then planted in 15-cm containers. Plants had been growing for about 16 weeks when the photographs and the description were taken. In the following description, color references are made to The Royal Horticultural Society Colour Chart, 1995 Edition, except where general terms of ordinary dictionary significance are used.

Botanical classification: *Pentas lanceolata* cultivar Lava White.

Parentage:

*Female, or seed, parent.*—Unnamed proprietary selection of *Pentas lanceolata,* not patented.

*Male, or pollen, parent.*—Unnamed proprietary selection of *Pentas lanceolata,* not patented.

Propagation:

*Type cutting.*—Terminal cuttings.

*Time to initiate roots.*—About 10 to 14 days at 22° C.

*Time to produce a rooted young plant.*—About 28 days at 20° C.

*Root description.*—Fine; white in color.

*Rooting habit.*—Freely branching.

Plant description:

*General appearance.*—Upright and outwardly spreading plant habit; inverted triangle.

*Growth and branching habit.*—Moderately vigorous and freely-branching growth habit with about eight lateral branches per plant. Pinching, that is removal of the terminal apex, enhances branching potential.

*Plant height.*—About 25 cm.

*Plant diameter or spread.*—About 35 cm.

*Lateral branches.*—Length: About 18 cm. Diameter: About 5 mm. Internode length: About 4 cm. Texture: Pubescent. Color: 146A.

*Foliage description.*—Arrangement: Opposite, simple. Length: About 7 to 8 cm. Width: About 4.4 cm. Shape: Narrowly elliptical. Apex: Acute. Base: Acute to attenuate. Margin: Entire. Texture, upper and lower surfaces: Pubescent; coarse; rugose. Venation pattern: Pinnate. Color: Developing foliage, upper surface: 147A. Developing foliage, lower surface: 147B. Fully expanded foliage, upper surface: 147A. Fully expanded foliage, lower surface: 147C. Venation, upper surface: 147C. Venation, lower surface: 147C to 147D. Petiole: Length: About 1 cm. Diameter: About 2 mm. Texture, upper and lower surfaces: Pubescent. Color: 147C.

Flower description:

*Flower type and habit.*—Numerous salverform single flowers that are arranged on large terminal corymbs; about 75 flowers develop per corymb. Flowers face upright and outward. Inflorescences positioned above the foliage on erect peduncles. Flowers last about 10 to 14 days under greenhouse conditions. Flowers not persistent. Flowers not fragrant.

*Natural flowering season.*—In the garden, flowering is continuous through the spring and summer. In the greenhouse, flowering is continuous year-round.

*Inflorescence height.*—About 5 cm.

*Inflorescence diameter.*—About 9 by 11 cm.

*Flower height.*—About 3 cm.

*Flower diameter.*—About 2 cm.

*Flower tube length.*—About 2.2 cm.

*Flower throat diameter.*—About 6 mm.

*Flower tube diameter.*—About 1 mm.

*Flower buds* (*at stage of showing color*).—Length: About 1.5 cm. Diameter: About 2 mm. Shape: Elongated ovoid. Color: 155A.

*Petals.*—Quantity per flower/arrangement: Five to six in a single whorl; fused at base. Lobe length: About 7 mm. Lobe diameter: About 5 mm. Lobe shape: Elliptic. Lobe apex: Acute. Lobe base: Fused. Lobe margin: Entire. Texture, upper and lower surfaces: Smooth, glabrous; velvety. Color: When opening and fully opened, upper surface: 155A. When opening and fully opened, lower surface: 155C. Throat: 155D. Tube: 155C.

*Sepals.*—Quantity per flower/arrangement: Five to six in a single whorl; fused at base. Length: About 3 to 5 mm. Width: About 1.5 to 3 mm. Shape: Elliptic. Apex: Acute. Base: Fused. Margin: Entire. Texture, upper and lower surfaces: Smooth, glabrous. Color, upper surface: 147A. Color, lower surface: 147B.

*Peduncles.*—Length: About 1.5 to 2.5 cm. Diameter: About 1.5 mm. Angle: Upright to about 45° from vertical. Strength: Strong. Texture: Pubescent. Color: 146A.

*Pedicels.*—Length: About 3 to 6 mm. Diameter: Less than 1 mm. Angle: Upright to about 45° from vertical. Strength: Strong. Texture: Pubescent. Color: 146A.

*Reproductive organs.*—Stamens: Quantity per flower: Six. Anther size: About 1 mm by 3 mm. Anther shape: Ovoid. Anther color: 155C. Pollen amount: Scarce. Pollen color: 155C. Pistils: Quantity per flower: One. Pistil length: About 2.6 mm. Stigma shape: Two-parted. Stigma color: 155C. Style length: About 2.3 mm. Style color: 155C. Ovary color: 145C.

*Seed/fruit.*—Seed and fruit production have not been observed.

Disease/pest resistance: Plants of the new *Pentas* have not been observed to be resistant to pathogens and pests common to *Pentas.*

It is claimed:

1. A new and distinct cultivar of *Pentas* plant named 'Lava White', as illustrated and described.

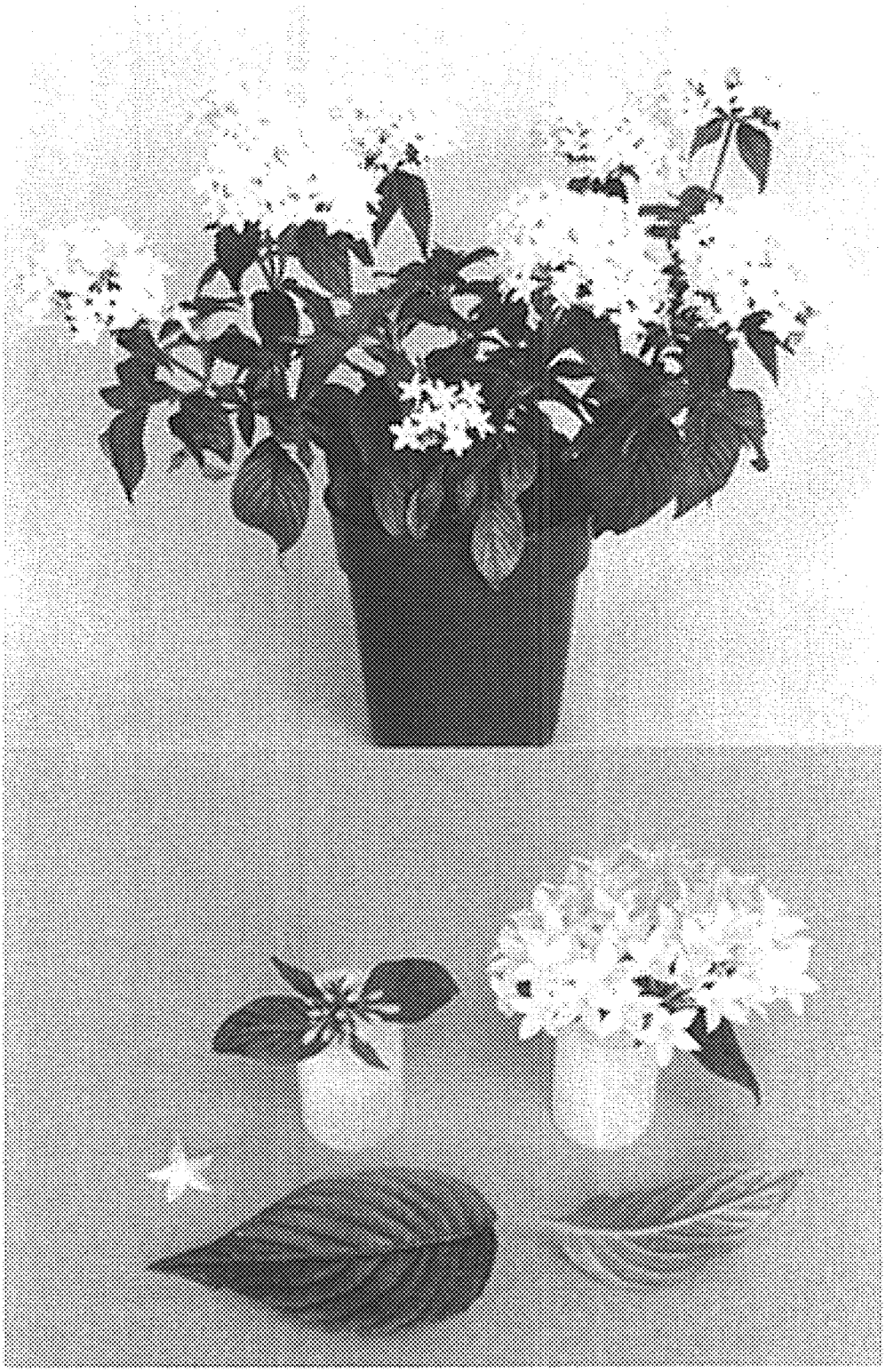

* * * * *